United States Patent [19]

Imai

[11] Patent Number: 5,702,922
[45] Date of Patent: Dec. 30, 1997

[54] METHOD FOR THE EXTRACTION OF GLICENTIN OR GLICENTIN ANALOGOUS SUBSTANCES

[75] Inventor: Shinjirou Imai, Ohimachi, Japan

[73] Assignee: Nisshin Flour Milling Co., Ltd., Tokyo, Japan

[21] Appl. No.: 562,148

[22] Filed: Nov. 22, 1995

[30] Foreign Application Priority Data

Nov. 29, 1994 [JP] Japan ................................ 6-294180

[51] Int. Cl.$^6$ ........................... C12P 21/04; A61K 38/00
[52] U.S. Cl. ...................... 435/71.2; 435/71.1; 514/12; 530/324
[58] Field of Search ........................ 435/71.1, 71.2; 514/12; 530/324

[56] References Cited

U.S. PATENT DOCUMENTS 5,432,156  7/1995  Matsuno et al. ...................... 514/12

FOREIGN PATENT DOCUMENTS

| 0 586 812 | 3/1994 | European Pat. Off. . |
| 0 612 531 | 8/1994 | European Pat. Off. . |
| 0 635 573 | 1/1995 | European Pat. Off. . |
| 0 662 482 | 7/1995 | European Pat. Off. . |

*Primary Examiner*—David M. Naff
*Assistant Examiner*—Deborah K. Ware
*Attorney, Agent, or Firm*—Oblon, Spivak, McClelland, Maier & Neustadt, P.C.

[57] ABSTRACT

In the method for the extraction of glicentin or a glicentin analogous substance from the cells of a transformed microorganism having incorporated therein an expressible gene encoding glicentin or a glicentin analogous substance, the extraction is carried out using an aqueous solution of an inorganic acid and/or an organic acid. The glicentin is human glicentin or a human glicentin analogous substance.

26 Claims, 3 Drawing Sheets

METHOD FOR THE EXTRACTION OF GLICENTIN OR GLICENTIN ANALOGOUS SUBSTANCES

FIELD OF THE INVENTION

This invention relates to an improved method for the extraction of glicentin or glicentin analogous substances from the cells of transformed microorganisms.

BACKGROUND OF THE INVENTION

In producing proteins or peptides by microorganisms according to recombinant gene technology, it is said that the desired products (i.e. microbially produced proteins or peptides) are present in the cytoplasm of microorganisms. The methods of extracting the desired products in the cytoplasm from the cells of microorganisms by breaking the cell walls and membranes include mechanical, enzymatic methods and a combination thereof. Mechanical disruption methods are by ultrasonic wave and by French press. However, they are disadvantageous in that all intracellular components in the cells of microorganisms may be transferred into an extract, which results in the contamination by various impurities of other proteins than the desired products. The disruption of the walls and membranes in the cells of microorganisms brings about heat generation which may adversely affect the desired products. For instance, EPA 662 482 discloses a method for preparing a glicentin fused peptide from *Escherichia coli* wherein the transformed *E. coli* is sonificated and a supernatant is collected by centrifugation to obtain cell extracts of *E. coli*. The cell extracts may be contaminated with a wide variety of impurities. This requires many purification steps which include thiopropyl-Sepharose column chromatography, salting-out with ammonium sulfate, a gel filtration column chromatography and a cation exchange resin chromatography.

In enzymatic methods, enzymes capable of decomposing the cell walls and membranes in the microorganism have been selected for the subject microorganisms. For instance, zymolyase is used for yeast and lysozyme is for *E. coli*. However, those enzymes are often contaminated with proteolytic enzymes so that the desired products may frequently undergo decomposition. Even if a pure enzyme free from any proteolytic enzyme is used, the desired product may be frequently decomposed with any proteolytic enzyme as originally contained in the microorganism itself under the reaction condition of the enzyme.

In addition to the above-mentioned methods, there is an extraction method using strong denaturing agents such as urea, guanidine hydrochloride or detergents. However, this method provides the proteins with very high solubility in urea or guanidine hydrochloride, which presents the problem that other proteins are contained in the extract together with the desired products and also the problem that the desired products may be denatured.

As discussed above, the prior art methods of extracting the microbially produced proteins or peptides are not absolutely satisfactory. This has required an improved extraction method in which glicentin or a glicentin analogous substance is produced by a transformed microorganism and it can be selectively extracted from the transformed microorganism without any unnecessary denaturation or decomposition.

SUMMARY OF THE INVENTION

The present inventors have found that glicentin or a glicentin analogous substance can be selectively and efficiently produced by extracting with an aqueous acid solution from the cells of a transformed microorganism having incorporated therein an expressible gene encoding glicentin or the glicentin analogous substance, without any disruption of the cells and any denaturation and decomposition of protein.

The present invention provides a method for the extraction of glicentin or a glicentin analogous substance from the cells of a transformed microorganism having incorporated therein an expressible gene encoding glicentin or the glicentin analogous substance, the improvement in which the extraction is carried out using an aqueous acid solution.

In a preferred embodiment of the invention, the cell wall and membrane in the cells of the transformed microorganism are pre-treated with an aqueous acid solution without any disruption of the cell pellet, and subsequently the cell pellet is separated and extracted with an aqueous acid solution to obtain glicentin or the glicentin analogous substance.

DETAILED DESCRIPTION OF THE INVENTION

Figure 1:
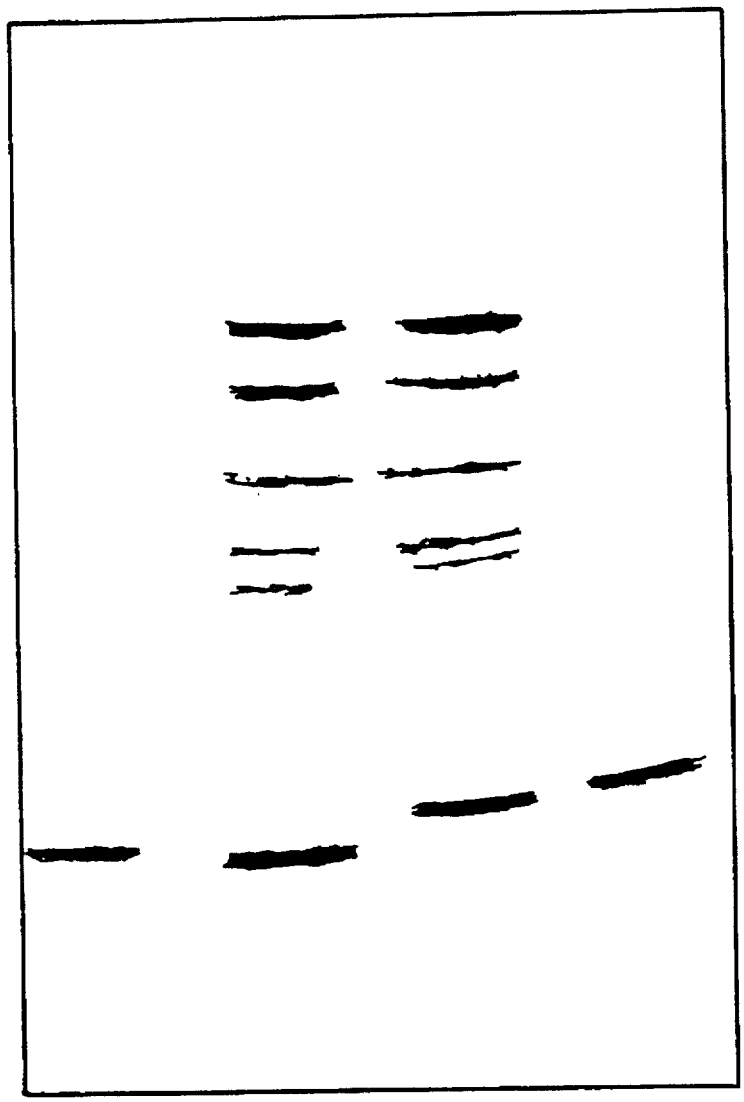
FIG. 1 is a figure illustrating the results from analysis of the extracts obtained in Example 1 and Comparative Examples 1 and 2 according to SDS polyacrylamide gel electrophoresis.

Glicentin of the invention is a known peptide comprising 69 amino acid residues. The activity of stimulating insulin secretion is known in EPA 586 812, and the activities of proliferating an intestinal mucosa and increasing intestinal villus height are known in EPA 612 531.

The term "glicentin analogous substance" as used herein refers to a peptide comprising partially an entire amino acid sequence of glicentin, or a peptide comprising 29 or more amino acid residues of an entire amino acid sequence of glicentin.

Representative example of the former peptide includes glicentin precursors which are converted by an enzymatic or non-enzymatic processing to glicentin or glicentin derivatives as a prodrug for effective production of glicentin or for providing an improved absorption in a living body.

Examples of glicentin precursors include glicentin fused peptides wherein an amino acid or a peptide chain is bound to glicentin at the N-terminus and/or C-terminus thereof, e.g. those disclosed in EPA 635,573, which include the following peptides:

Met-A-glicentin wherein Met represents methionine encoded by the translation initiation codon ATG and A represents a peptide consisting of an even number of amino acids, the amino terminus of which is selected from alanine, glycine, serine, valine or threonine and Met-B-glicentin wherein Met is as defined above and B represents either an amino acid selected from arginine, asparagine, aspartic acid, glutamine, glutamic acid, isoleucine, leucine, lysine, tryptophan, tyrosine, phenylalanine or histidine, or a peptide consisting of an odd number of amino acid, the amino terminus of which is selected from arginine, asparagine, aspartic acid, glutamine, glutamic acid, isoleucine, leucine, lysine, tryptophan, tyrosine, phenylalanine or histidine and further glicentin fused peptides disclosed in EPA 662,482, e.g., human glicentin fused peptides wherein the peptide moiety connected to the N-terminus of human glicentin has even-numbered amino acids and the fused peptide is the peptide containing cysteine at the 1st and/or the 2nd positions to the amino terminal direction of the fused peptide from the N-terminus of human glicentin and human glicentin fused peptides wherein the peptide moiety connected to the N-terminus of human glicentin has even-numbered amino acids and the fused peptide is the peptide containing one or plural numbers of arginine and/or lysine at the odd-numbered positions to the amino-terminal direction of the fused protein from the N-terminus of human glicentin.

Examples of peptides comprising 29 or more amino acid residues of an entire amino acid sequence of glicentin include, e.g., glicentin (1–61) composed of the 1st to 61st amino acid residues of an entire sequence of glicentin; glicentin (1–30) composed of the 1st to 30th amino acid residues of an entire sequence of glicentin, i.e., glicentin related polypeptide (GRPP); glicentin (33–69) composed of the 33rd to 69th amino acid residues of an entire sequence of glicentin, i.e., oxintomodulin; and glicentin (33–61) composed of the 33rd to 61st amino acid residues of the entire sequence of glicentin, i.e., glucagon.

Those glicentin analogous substances may also be glicentin derivatives wherein one or several amino acids of glicentin are replaced by other amino acids.

Microorganisms which can be used in the transformation are any microorganism being capable of producing glicentin or glicentin analogous substances in high yield, and preferred are gram-negative bacteria such as E. coli, e.g., E. coli G662 disclosed in EPA 662 482.

In the method of the present invention, any acid can be used in the form of the aqueous solution if it can give a pH of not more than 3 at the concentration applied and it does not bring about denaturation, decomposition and modification of the desired product (i.e., glicentin or a glicentin analogous substance) under the condition applied.

Examples of acids include an inorganic acid such as hydrochloric acid, sulfuric acid or phosphoric acid; an organic acid such as acetic acid or formic acid; and a mixture of two or more acids. Inorganic acid is particularly preferable.

The concentration of the aqueous acid solution is preferably 10–1000 mM for the inorganic acids and 5–20% (w/w) for the organic acids. With the concentration of less than the lower limit, insufficient extraction is performed. With the concentration of higher than the upper limit, it is likely that glicentin or a glicentin analogous substance may undergo denaturation, decomposition and modification by the aqueous acid solution.

In the practice of this invention, the transformed microorganism having incorporated therein an expressible gene encoding glicentin or a glicentin analogous substance is incubated in a culture medium to give a microorganism. Incubation is carried out under such a condition that glicentin or a glicentin analogous substance can be accumulated within the cells of microorganism. The cell pellet of microorganism can be used even after cryopreservation or formation into its acetone powder, if glicentin or a glicentin analogous substance remains stable.

In the method of the present invention, it has been found that the treatment of the cell pellet of the microorganism with the aqueous solution of an inorganic acid such as hydrochloric acid or an organic acid such as acetic acid having the specified concentration results in dissolution of glicentin or a glicentin analogous substance in the aqueous acid solution and extraction from the cells, but other proteins derived from the cells of original microorganism remain insoluble. Accordingly, the method of the present invention permits a selective extraction of glicentin or a glicentin analogous substance without any modification and decomposition.

In the preferred embodiment of the present invention, as a pretreatment for selective extraction, 2 ml–10 ml of the aqueous acid solution is added to 1 g of the cell pellet of microorganism on a wet basis, the mixture is stirred for 5 minutes to 2 hours and then centrifuged or filtered to separate the cell pellet of microorganism. This procedure can remove the medium components and partly bacteriolyzed impurities. It is assumed that the cell membrane or wall of the incubated cells will undergo the change such as denaturation and remain insoluble.

In the pretreatment of the cell wall and membrane in the cells of microorganism with the aqueous acid solution, a concentration of the aqueous acid solution is preferably 10–100 mM for inorganic acids and 5–10% (w/w) for organic acids. At that time, the temperature is usually 0°–37° C., preferably 0°–10° C. An amount of the aqueous acid solution is preferably 2 ml–10 ml for 1 g of the cell pellet of microorganism on a wet basis. A period of time required for the treatment is usually 5 minutes to 2 hours, preferably 5–30 minutes.

For separation of the cell debris of microorganisms, centrifugation or filtration is preferably used. In filtration, if the treated cells of microorganism is of such a small size as E. coli, it is preferable to add 0.5–5.0% (w/w) of a filter aid such as Celite to the aqueous acid solution for facilitating filtration preferably by suction.

From the cell debris of microorganisms thus separated, glicentin or a glicentin analogous substance is extracted with the aqueous acid solution. An amount of the aqueous acid solution used for extraction is preferably at an equal or more level than that of the aqueous acid solution used for the above pretreatment. The acid concentration is also preferably equal or higher. Extraction with the aqueous acid solution is performed by adding the solution and then stirring. Subsequently, a supernatant is collected by centrifugation or filtration. The collected supernatant is immediately applied to the subsequent purification step. At this time, it is preferable to inhibit influence of the aqueous acid solution as low as possible by neutralization.

In the extraction treatment, a concentration of the aqueous acid solution is preferably 10–100 mM for an inorganic acid and 5–10% (w/w) for an organic acid. A temperature at this time is usually 0°–37° C., preferably 0°–10° C. An amount of the aqueous acid solution is 2 ml–10 ml for 1 g of the cell pellet of microorganism on a wet basis. A period of time required for extraction is usually 10 minutes to 8 hours, preferably 30 minutes to 2 hours, more preferably 30–60 minutes. Extraction efficiency increases with increasing parameters such as an extracted amount, a concentration of an extract solution and an extraction time. However, increased parameters may bring about the denaturation, decomposition, modification and others of glicentin or a glicentin analogous substance. For this reason, it is preferable to repeat the extraction at short intervals by portions with care, in order to reduce the exposure time of glicentin or a glicentin analogous substance to the aqueous acid solution as short as possible and to increase the extraction efficiency.

Following extraction, the cells treated in the above manner is separated by centrifugation or filtration.

According to the present method, glicentin or a glicentin analogous substance can be obtained in a highly purified form. In case that the desired product is contaminated with impurites such as low molecular substances (e.g., saccharides), any purification means can be used such as gel filtration chromatography or the like.

This invention is further illustrated by the following examples, in which E. coli G 662 disclosed in EPA 662,482 was used as the transformant capable of producing human glicentin fused peptide.

EXAMPLE 1

Production and incubation of E. coli G 662 were carried out in accordance with the process mentioned in EPA 662 482 to prepare a cultured cell pellet of G 662. Subsequently, a human glicentin fused peptide was extracted from the cultured cell pellet of G 662 in the following manner.

In 200 μl of 50 mM hydrochloric acid was suspended 100 mg of the cultured cell pellet on a wet basis. The suspension was immediately centrifuged (16000 G) for 5 minutes to remove a supernatant. The remaining cultured cell pellet was suspended in 1 ml of 100 mM hydrochloric acid, the suspension was allowed to stand at 4° C. for 15 minutes and then centrifuged (16000 G) for 5 minutes to obtain a supernatant. This solution was designated as the extract of this invention.

Comparative Example 1

The cultured cell pellet obtained in Example 1 was extracted by the prior art process using a cell membrane decomposing enzyme. More specifically, 100 mg of the cultured cell pellet on a wet basis was suspended in a 0.1M sodium borate solution (pH 8.0) containing 300 μg/ml of a cell membrane decomposing enzyme, albumin lysozyme (available from SEIKAGAKU KOGYO K.K.) and the suspension was maintained at room temperature for 15 minutes. This suspension was centrifuged (16000 G) for 5 minutes to obtain a supernatant. This solution was designated as Extract I according to the prior art process.

Comparative Example 2

The cultured cell pellet obtained in Example 1 was sonificated to break the cell pellet and extracted with urea. More specifically, 100 mg of the cultured cell pellet on a wet basis was suspended in 1 ml of a 8M aqueous solution of urea and sonificated for 1 minute to break the cells, and then centrifuged (16000 G) for 5 minutes to obtain a supernatant. This solution was designated as Extract II according to the prior art process.

Test Example 1

Each of the extracts obtained in Example 1 as well as Comparative Examples 1 and 2 was subjected to SDS polyacrylamide gel electrophoresis to determine an extraction efficiency of human glicentin fused peptides. The conditions for SDS polyacrylamide gel electrophoresis were as follows:
Electrophoresis apparatus: Pharmacia First System
Gel: 20% Homogeneous Gel
Staining: Coomassie Brilliant Blue staining The human glicentin fused peptide obtained by the method described in EPA 662 482 was used as a standard. The results are shown in FIG. 1. In FIG. 1, lane 1 indicates the band of the extract according to this invention, lane 2 does the band of Extract I according to the prior art process, lane 3 does the band of Extract II according to the prior art process and lane 4 does the band of the standard human glicentin fused peptide.

The main band of Extract I in lane 2 indicates more increased mobility with more decreased molecular weight, as compared with the standard human glicentin fused peptide in lane 4. It was confirmed that a wide variety of other bands than the main band were observed and a large amount of impurities was found. The main band of Extract II in lane 3 shows the same mobility as that of the standard human glicentin fused peptide, but a large number of the bands for impurities was confirmed. On the other hand, only the band having the same mobility as that of the standard human glicentin fused peptide was found in lane 1 wherein the extract of this invention was flown, which indicates that there is no substantial contamination with polymeric impurities.

This shows that the present method can provide an extract of a remarkably higher purity without any enzymatic decomposition as compared with other methods.

Test Example 2

The human glicentin fused peptide obtained in Example 1 was determined by the following procedure.

Figure 2:
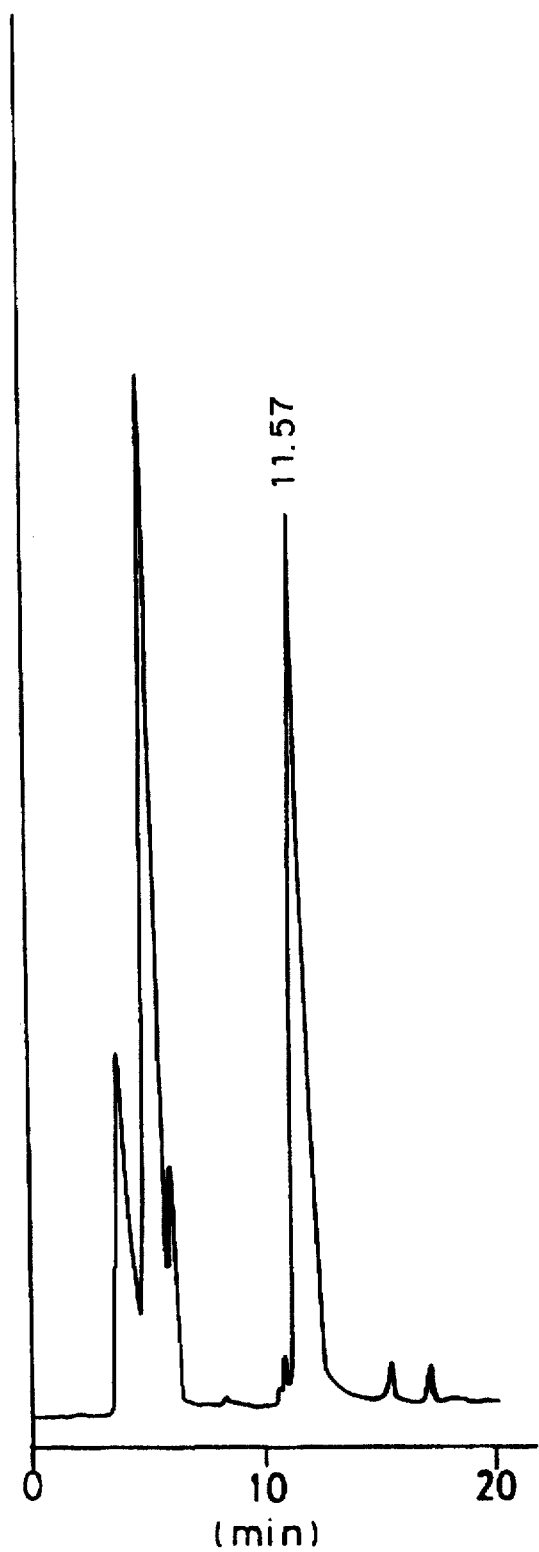
FIG. 2 is a chromatogram obtained by a high-speed liquid chromatography of human glicentin fused peptide obtained in Example 1.

To 0.5 ml of the extract was added 4.5 ml of 10 mM hydrochloric acid, the mixture was stirred and centrifuged (20000 G) for 10 minutes to obtain a supernatant. 0.5 ml of the supernatant was subjected to a high-speed liquid chromatography (HPLC). The conditions for HPLC were as follows:

| Column: | Inertsil ODS (5 μm, 4.6 mmφ × 250 mm) available from GL Science, flow rate 1 ml/min. |
|---|---|
| Gradient: | Linear gradient from Solution A to Solution B over a period of 20 minutes |
| Elution: | Solution A |
| | 20% acetonitrile + 2 mM hydrochloric acid |
| | Solution B |
| | 40% acetonitrile + 2 mM hydrochloric acid |
| Detection: | UV absorption at 220 nm |
| Apparatus: | Manufactured by Hitachi Co., Ltd. An HPLC chromatogram is shown in FIG. 2. |

The human glicentin fused peptide obtained in Comparative Example 2 was determined in the same manner as described above. An HPLC chromatogram is shown in FIG. 3.

The HPLC chromatograms of the human glicentin fused peptides obtained in Example 1 and Comparative Example 2 were analyzed by the following method.

Analysis was performed by means of D-2500 chromato-integrator manufactured by Hitachi Co., Ltd. An extracted amount of human glicentin fused peptide was calculated from the peak area of the same retention time, based on the peak area obtained when 25 μg of the standard human glicentin fused peptide was loaded onto HPLC under the same condition.

Figure 3:
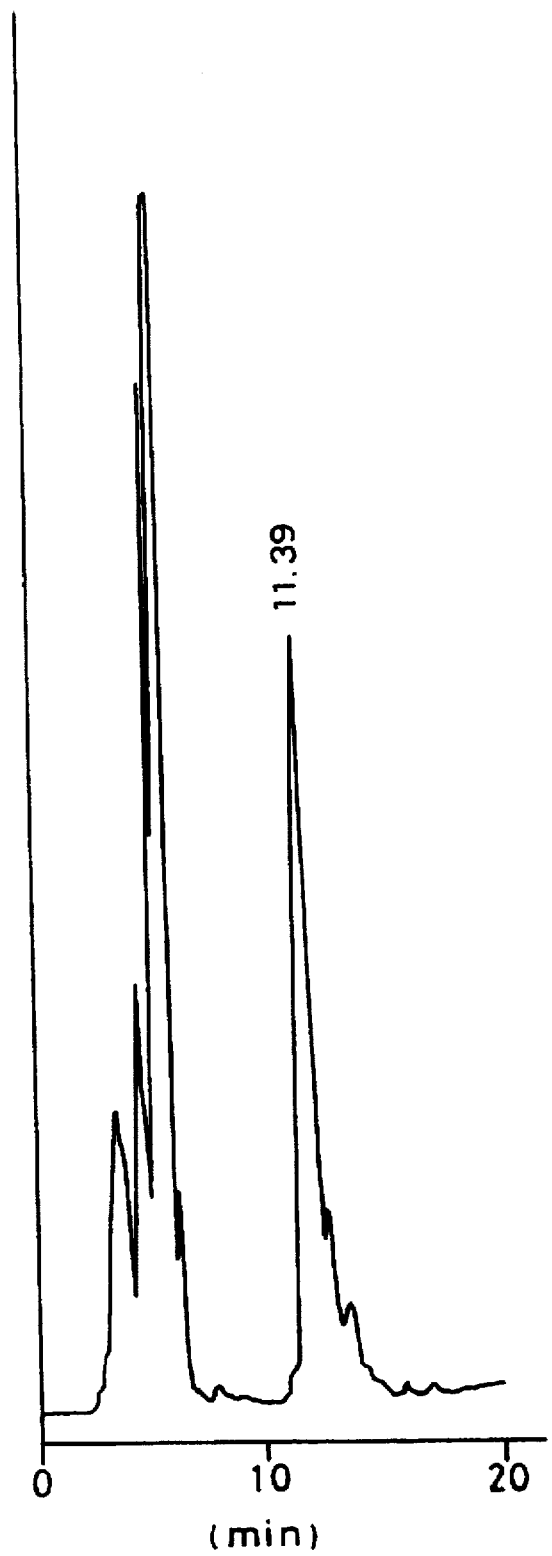
FIG. 3 is a chromatogram obtained by a high-speed liquid chromatography of human glicentin fused peptide obtained in Comparative Example 2.

An extracted amount of the human glicentin fused peptide in Extract II obtained in Comparative Example 2 was 1.06 mg per 1 ml of the extract as calculated from the peak area of 11.39 min. shown in FIG. 3. On the other hand, an extracted amount of the human glicentin fused peptide in Extract I obtained in Example 1 was 1.24 mg per 1 ml of the extract as calculated from the peak area of 11.57 min. shown in FIG. 2. This indicates that the present method is superior to the prior art processes in regard to the extracted amount of the desired peptide product.

Example 2

100 mg of the cultured cell pellet on a wet basis was suspended in 200 μl of each of the following aqueous acid solutions:

0.1N (100 mM) hydrochloric acid,
0.1N (50 mM) sulfuric acid,
0.5N (167 mM) phosphoric acid and
10% (w/w) acetic acid The suspension was immediately centrifuged (16000 G) for 5 minutes to remove a supernatant. Subsequently, the remaining cultured cell pellet was suspended in 1 ml of the same aqueous acid solution and the suspension was allowed to stand at 4° C. for 15 minutes and centrifuged (16000 G) for 5 minutes to obtain a supernatant.

A concentration of the human glicentin fused peptide in the supernatant was determined by HPLC as used in Test Example 2. The results are shown in Table 1, in which the extracted amount refers to a weight of the human glicentin fused peptide in 1 ml of the extract obtained from 100 mg of the cultured cell pellet on a wet basis.

TABLE 1

| Acid | Extracted amount (μg) |
| --- | --- |
| 100 mM hydrochloric acid | 1235 |
| 50 mM sulfuric acid | 777 |
| 167 mM phosphoric acid | 1291 |
| 10% (w/w) acetic acid | 241 |

The results in Table 1 indicate that the extracted amounts of human glicentin fused peptide are different depending upon the sort of the aqueous acid solutions used, but extraction is performed by any aqueous acid solution, and also that each sort of aqueous acid solutions can be used in the extraction of glicentin or a glicentin analogous substance by varying a concentration of the aqueous acid solution correspondingly to the sort of the aqueous acid solution. It can be seen that an inorganic acid, particularly hydrochloric acid or phosphoric acid is preferable.

Test Example 3

Comparison of extracted amounts by aqueous acid solutions with varying concentrations 100 mg of the cultured cell pellet on a wet basis was suspended in 200 μl of 0.05N (50 ml) of hydrochloric acid and the suspension was immediately centrifuged (16000 G) for 5 minutes to remove a supernatant. Then, the remaining cultured cell pellet was suspended in 1 ml of each of 0.001N–3N (1 mM–3000 mM) hydrochloric acid, the suspension was allowed to stand at 4° C. for 15 minutes and centrifuged (16000 G) for 5 minutes to obtain a supernatant.

An extracted amount of the human glicentin fused peptide in the above supernatant was determined by HPLC described in Test Example 2. The results are shown in Table 2, in which the extracted amount refers to a weight of the human glicentin fused peptide in 1 ml of the extract obtained from 100 mg of the cultured cell pellet on a wet basis.

TABLE 2

| Concentration of HCl | | Extracted amount |
| --- | --- | --- |
| (N) | (mM) | (μg) |
| 0.001 | 1 | 0 |
| 0.003 | 3 | 0 |
| 0.01 | 10 | 301 |
| 0.03 | 30 | 790 |
| 0.1 | 100 | 1203 |
| 0.3 | 300 | 1100 |
| 1 | 1000 | 551 |
| 3 | 3000 | 236 |

When extraction was performed with 3N hydrochloric acid, the extract was colored and was confirmed to contain the decomposition product of human glicentin fused peptide, which was not acceptable.

The above results indicate that the extraction of human glicentin fused peptide was well performed with hydrochloric acid at a concentration range of 0.01N–1N (10 mM–1000 mM).

Test Example 4

100 mg of the cultured cell pellet was suspended in 200 μl of 0.1N (33 mM) of phosphoric acid and the suspension was immediately centrifuged (16000 G) for 5 minutes to remove a supernatant. Then, the remaining cultured cell pellet was suspended in 1 ml of each of 0.001N–3N (0.3 mM–1000 mM) phosphoric acid and the suspension was allowed to stand at 4° C. for 15 minutes and centrifuged (16000 G) for 5 minutes to obtain a supernatant.

An extracted amount of the human glicentin fused peptide in the above supernatant was determined by HPLC described in Test Example 2. The results are shown in Table 3, in which the extracted amount refers to a weight of the human glicentin fused peptide in 1 ml of the extract obtained from 100 mg of the cultured cell pellet on a wet basis.

TABLE 3

| Concentration of $H_3PO_4$ | | Extracted amount |
| --- | --- | --- |
| (N) | (mM) | (μg) |
| 0.001 | 0.3 | 0 |
| 0.003 | 1 | 0 |
| 0.01 | 3 | 0 |
| 0.03 | 10 | 70 |
| 0.1 | 33 | 808 |
| 0.3 | 100 | 1285 |
| 1 | 333 | 1366 |
| 3 | 1000 | 1252 |

The above results indicate that the extraction of human glicentin fused peptide was well performed with phosphoric acid at a concentration range of 0.03N–3N (10 mM–1000 mM).

What is claimed is:

1. A method for the extraction of glicentin or a glicentin analogous substance from the cells of a transformed microorganism having incorporated therein an expressible gene encoding glicentin or the glicentin analogous substance, which comprises:
   a) extracting said glicentin or glicentin analogous substance from said cells with an aqueous acidic solution; and
   b) isolating said glicentin or said glicentin analogous substance.

2. The method of claim 1, wherein said glicentin is human glicentin and said glicentin analogous substance is a human glicentin analogous substance.

3. The method of claim 1, wherein the glicentin analogous substance is a peptide comprising 29 or more amino acid residues of an entire amino acid sequence of glicentin.

4. The method of claim 1, wherein the aqueous acid solution is an aqueous solution comprising an inorganic acid or an organic acid or both.

5. The method of claim 4, wherein the inorganic acid is selected from the group consisting of hydrochloric acid and phosphoric acid.

6. The method of claim 4, wherein the aqueous acid solution has a pH of not more than 3 and the inorganic acid has a concentration of from about 10 to 1,000 mM.

7. The method of claim 4, wherein the organic acid is acetic acid.

8. The method of claim 4, wherein the aqueous acid solution has a pH of not more than 3 and the organic acid has a concentration of about 5 to 20% (w/w).

9. The method of claim 1, wherein said transformed microorganism is a gram-negative bacterium.

10. The method of claim 9, wherein said transformed microorganism is E. coli.

11. The method of claim 1, wherein said glicentin analogous substance comprises a sequence composed of the 1st to 61st amino acid residues of glicentin, a sequence composed of the 1st to 30th amino acid residues of glicentin, a sequence composed of the 33rd to 69th amino acid residues of glicentin or a sequence composed of the 33rd to 61th amino acid residues of glicentin.

12. The method of claim 1, wherein said extraction is effected at about 0° to 37° C.

13. The method of claim 12, wherein said extraction is effected at about 0° to 10° C.

14. A method for the extraction of glicentin or a glicentin analogous substance from the cells of a transformed microorganism having incorporated therein an expressible gene encoding the glicentin or the glicentin analogous substance, which comprises:
 a) pretreating the cells of the transformed microorganism with an aqueous acid solution;
 b) separating cell debris and extracting said glicentin or said glicentin analogous substance with the aqueous acid solution; and
 c) isolating said glicentin or said glicentin analogous substance.

15. The method of claim 14, wherein said glicentin is human glicentin and said glicentin analogous substance is a human glicentin analogous substance.

16. The method of claim 14, wherein the glicentin analogous substance is a peptide comprising 29 or more amino acid residues of an entire amino acid sequence of glicentin.

17. The method of claim 14, wherein the aqueous acid solution is an aqueous solution comprising an inorganic acid or an organic acid or both.

18. The method of claim 17, wherein the inorganic acid is selected from the group consisting of hydrochloric acid and phosphoric acid.

19. The method of claim 17, wherein the aqueous acid solution has a pH of not more than 3 and the inorganic acid has a concentration of from about 10 to 1,000 mm.

20. The method of claim 17, wherein the organic acid is acetic acid.

21. The method of claim 17, wherein the aqueous acid solution has a pH of not more than 3 and the organic acid has a concentration of about 5 to 20% (w/w).

22. The method of claim 14, wherein said transformed microorganism is a gram-negative bacterium.

23. The method of claim 22, wherein said transformed microorganism is E. coli.

24. The method of claim 14, wherein said glicentin analogous substance comprises a sequence-composed of the 1st to 61st amino acid residues of glicentin, a sequence composed of the 1st to 30th amino acid residues of glicentin, a sequence composed of the 33rd to 69th amino acid residues of glicentin or a sequence composed of the 33rd to 61th amino acid residues of glicentin.

25. The method of claim 14, wherein said extraction is effected at about 0° to 37° C.

26. The method of claim 25, wherein said extraction is effected at about 0° to 10° C.

* * * * *